United States Patent [19]

Rapisarda

[11] Patent Number: 5,314,881
[45] Date of Patent: May 24, 1994

[54] USE OF PHOSPHOMYCIN AND THE PHARMACEUTICALLY ACCEPTABLE SALTS THEREOF AS A TOPICAL CICATRIZER

[75] Inventor: Nunzio Rapisarda, Via Duca Abruzzi 10, Palagonia-Catania, Italy

[73] Assignees: Nunzio Rapisarda, Palagonia Catania; Francia Farmaceutici Industria Farmaco-Biologica S.R.L., Milan; Salvatore Pignataro, Catania, all of Italy; a part interest

[21] Appl. No.: 19,345

[22] Filed: Feb. 18, 1993

Related U.S. Application Data

[63] Continuation of Ser. No. 729,541, Jul. 15, 1991, abandoned.

[30] Foreign Application Priority Data

Jul. 31, 1990 [IT] Italy ................. 21138 A/90

[51] Int. Cl.$^5$ ........................... A61K 31/665
[52] U.S. Cl. ........................................ 514/99
[58] Field of Search ........................... 514/99

[56] References Cited

U.S. PATENT DOCUMENTS 3,914,231 10/1975 Hendlin et al. .............. 514/99 X
4,129,660 12/1978 Warolin et al. ............... 514/99

FOREIGN PATENT DOCUMENTS 2102811 2/1983 United Kingdom .

OTHER PUBLICATIONS

Dialog Information Services, AN-5788569, Aug. 1985, T. Nakamura, et al., "Clinical Studies on Fosfomycin Sodium Following Intravenous Administration (Tissue Conception and Clinical Efficacy)".
Arch. Derm. Forsch. vol. 246, 1973, pp. 27-34; W. Raab et al.: "Untersuchungen zur lokalen Anwendbarkeit von Phosphonomycin" *p. 28, lines 1-7; pp. 32-33*.
Drugs Exptl. Clin. Res:, vol. 7 No. 2, 1981, pp. 109-113; R. Germiniani et al. "Prophylaxis of surgical wound infections: comparison between three different regimens": *p. 111, left-hand column, lines 5-18; p. 112, left-hand column, 23-right-hand column, line 2*.
Japanese Journal of Antibiotics, vol. 32, No. 2, 1979, pp. 180-190; T. Koeda et al.; "General pharmacological studies on fosfomycin sodium" *pp. 190, 188-189; p. 186, table 2*.
W. Raab et al, "Untersuchungen Zur Lokalen Anwendbarkeit Von Phosphonomycin," Archives for Dermatological Research, vol. 246, No. 1 (1973) (With Partial English Translation).
The Japanese Journal of Antibiotics XXXII-2, Abstract and Conclusions (English Translation), p. 190, 1979.
The Japanese Journal of Antibiotics, vol. 42, No. 1, 1989, pp. 179-188 H. Takahashi et al.: "Use of fosfomycin tablets in the treatment of purulent skin diseases" *p. 188*.

Primary Examiner—Jerome D. Goldberg
Assistant Examiner—Phyllis G. Spivack
Attorney, Agent, or Firm—Oblon, Spivak, McClelland, Maier & Neustadt

[57] ABSTRACT

Phosphomycin and pharmaceutically acceptable salts thereof topically used as cicatrizing agents.

6 Claims, No Drawings

USE OF PHOSPHOMYCIN AND THE PHARMACEUTICALLY ACCEPTABLE SALTS THEREOF AS A TOPICAL CICATRIZER

This application is a continuation of application Ser. No. 07/729,541, filed on Jul. 15, 1991, now abandoned.

The term cicatrization represents an ordered sequence of events directed to the healing of a breach of tissue which culminates with the formation of a scar; consequently, the term cicatrizer represents a substance which promotes or accelerates the healing of wounds.

The cicatrizers are a therapeutical class to which substances of Various nature belong, such as protective substances, that is substances that are in a measure of forming films suitable for providing a shelter for the wound without thereby occluding it, for example polyvinyl alcohol (FR-A-2566270) and certain synthetic polymers (GB 2060381), anti-congestive agents, such as chondroitin sulfate B (EP 097625), antiinflammatory agents, such as glycirrhetinic acid and its derivatives (GB 2122893) and the extract of arnica (FR-A-2504009), methabolism activators, such as coenzyme Q10 (U.S. Pat. No. 4,654,373), the biostimulines, retinol and its salts (EP 038246), somatotropin and its derivatives and cofactors (WO-A-8800207), vasodilatory agents, such as nicotinic acid, acetylcholine and benzylimidazoline, disinfectants and antibiotics.

The above-mentioned substances have actually a cicatrization adjuvant action, but do not directly take part in the mechanisms that are in charge of repairing the tissues, and among them the antibiotics known for this use essentially have the function of preventing the wound, lacking its normal natural defences, from being infected.

Phosphomycin, i.e. (−)cis-(1,2epoxypropyl)phosphonic acid, is an antibiotic described in U.S. Pat. No. 3,914,231 and is used in the therapeutical field as a systemic antibacterial agent since it is active against both gram-positive and gram-negative bacteria.

There has now been surprisingly discovered that phosphomycin and the pharmaceutically acceptable salts thereof develop an outstanding, absolutely unexpected cicatrizing activity when administered by a topical route. Such a novel therapeutical activity can in no way be related to the known antibiotic properties of the drug, but it is certainly related to an unexpected biochemical action that phosphomycin and its salts exhibit in an evident and surprising way.

The object of the present invention is therefore the use of phosphomycin, or a pharmaceutically acceptable salt thereof, by topical route as a cicatrizing agent.

An especially preferred salt of phosphomycin is the sodium salt.

The concentration of phosphomycin or its salt derivative in the medicament to be applied onto the wound can range from 100% to about 0.5%, the higher the drug concentration, the greater being the effectiveness of the medicament, the fact being thereby to be kept in mind that, even if the medicament contains 100% phosphomycin, it gives rise to no side-effects at a topical level or a systemic level. Phosphomycin or a salt derivative thereof, preferably the sodium salt, is topically applied in form of a dusting powder, but also in such pharmaceutical forms as lotions, gels, ointments, cremes, tablets for topical use, sprays, impregnated gauzes, sponges of a suitable material, such as fibrinogen.

To the formulation there can obviously be added further substances, such as antimycotic, antiviral, antipruriginous agents, absorbent substances, deodorizers, emollients, vitamins, amino-acids and so on, either of natural or synthetic origin.

Experimental studies carried out to the purpose of ascertaining the precise cicatrizing activity of phosphomycin have demonstrated that the drug stimulates the hemostasis, with a consequent reduction of inflammation, performs a precise function in angiogenesis, i.e. the regeneration of the blood vessels, displays a chemotactic action on the monocytes and fibroblasts, thereby providing a support for the fibroblastic proliferation and the granulation tissue. In particular, its action gives rise to an in situ increase of plasmatic fibronectin and of the number of macrophages that produce tissue fibronectin, fibronectin being a glycoprotein that is deeply involved in chemotaxis phenomena, opsonizations and methabolic processes concerning the connective tissue.

This novel activity of phosphomycin is therefore surprising not only in view of its well known antibiotic characteristics, but also because no one of the so-called cicatrizing drugs previously used ever exhibited an intervention at this level, that can be considered as one of the main stages of the cicatrization phenomenon.

In view of the above, phosphomycin, or a pharmaceutically acceptable salt thereof, can be put to the therapeutical use in the treatment of traumatic lesions, with loss of substance, surgery wounds with delayed healing or dehiscence of the suture, fibropathic ulcers, mammal abscesses, sacrococcigeal abscesses, burns.

A complete healing has been observed in all the cases treated with phosphomycin or its salt derivatives, including the cases that would usually have required surgery.

To confirm that the therapeutical cicatrizing action of phosphomycin can in no way be related to its antibiotic activity, experimental work has been carried out also with known antibiotics for the topical application, such as neomicin, bacitracin, sulfadiazine, either alone or in association. None of the comparison antibiotics tested has shown an activity that may be compared with that of phosphomycin, which, used alone, is able of inducing a complete healing of trauma.

Clinical experimentation examples will now be provided that better illustrate the cicatrizing activity of phosphomycin and provide a comparison with antibiotics known in the field.

TEST EXAMPLE 1

Thirty patients with surgery wounds arising from operations of various severity and kind, and that had not healed up within the usual time, or that had dehiscence of part of the suture with the consequent formation of a suppuration pouch, have been subjected, after regular drainage of the purulent mass, to the daily application of pure sodium phosphomycin in the form of a sterile powder.

The drug has been dusted directly on to the wound in a homogeneous distribution covering the whole of the injured area and kept in place with a sterile gauze protection.

After a two days therapy, all the treated wounds clearly exhibited the typical improvement signs of the cicatrization process, namely with a lively proliferation of the granulation tissue. The clinical healing has been noted for all the wounds of various kind within seven days of therapy with sodium phosphomycin alone, topically applied

TEST EXAMPLE 2

Fifty cases of wounds with loss of substance caused by various traumas have been randomly divided into two groups, only providing for equally dividing between the two groups wounds of a similar severity. The wounds of both groups were cleansed daily with sterile water.

The wounds of the first group of 25 cases were treated by homogeneously and completely dusting them with a commercially available product containing as the active ingredients neomicin sulfate (3300 IU), bacitracin zinc (250 IU), L-cysteine (2 mg), DL-threonine (1 mg), glycine (10 mg). Said treatment was repeated twice a day, always removing the sterile covering, according to the directions for use supplied with said composition. The clinical healing of the wounds of this group has been noted between the 7th and 25th treatment day.

The wounds of the second group of 25 cases were treated with pure, sterile sodium phosphomycin, carefully providing for the whole wound to be homogeneously covered with the drug, which in turn was kept in place by means of a sterile gauze. The clinical healing has been noted between the 3rd and the 10th day of treatment.

No other topical or sistemic therapy has been carried out contemporaneously.

The following examples are non limiting drug formulations examples.

FORMULATION EXAMPLE 1

| 100% phosphomycin dusting powder Sodium phosphomycin, sterile | 5 g |
|---|---|

FORMULATION EXAMPLE 2

| Dusting powder comprising: | |
|---|---|
| Sodium phosphomycin, sterile | 0,5 g |
| Kaolin bolus alba, sterile | 99 g |

FORMULATION EXAMPLE 3

Preparation for recombination location comprising:

| Sodium phosphomycin, sterile | 0,5 g |
|---|---|
| Distilled water, sterile | 30 ml |

The drug is introduced into a membrane stopper closing a 30 ml ampule filled with sterile distilled water. At the moment of use, a light pressure is applied to the stopper, thereby causing the powder contained therein to be mixed with water, and the resulting solution is used for the treatment.

FORMULATION EXAMPLE 4

Dressed gauze.

Each gauze is impregnated with phosphomycin dissolved in a suitable amount of propylene glycol.

FORMULATION EXAMPLE 5

| Ointment: 100 g of ointment contain | |
|---|---|
| Phosphomycin | 10 g |
| Yellow vaseline | 75 g |
| Lanolin anhydrous | 3 g |
| Wool wax | 2 g |
| Light mineral oil | 10 g |

I claim:
1. A method of promoting or accelerating wound healing in a patient in need thereof, comprising covering the whole of said wound with a powder consisting essentially of an amount of a pharmaceutically acceptable salt of phosphomycin effective to promote or accelerate said wound healing.
2. The method of claim 1, wherein said pharmaceutically acceptable salt of phosphomycin is sodium phosphomycin.
3. The method of claim 1, wherein said composition further consisting essentially of a pharmaceutically acceptable excipient.
4. The method of claim 2, said method further comprising, after said topically administering step, covering said wound with gauze.
5. The method of claim 2, wherein from 0.5 to 5 g of said sodium phosphomycin is topically administered twice a day for a period of time of from 3 to 10 days.
6. The method of claim 4, wherein from 0.5 to 5 g of said sodium phosphomycin is topically administered twice a day for a period of time of from 3 to 10 days.

* * * * *